United States Patent
Wu et al.

(10) Patent No.: US 9,352,014 B2
(45) Date of Patent: May 31, 2016

(54) CYCLOSPORIN A FORM 2 AND METHOD OF MAKING SAME

(71) Applicant: Allergan, Inc., Irvine, CA (US)

(72) Inventors: Ke Wu, Irvine, CA (US); Scott W. Smith, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/309,547

(22) Filed: Jun. 19, 2014

(65) Prior Publication Data

US 2014/0303343 A1 Oct. 9, 2014

Related U.S. Application Data

(62) Division of application No. 13/676,339, filed on Nov. 14, 2012, now Pat. No. 8,796,221.

(60) Provisional application No. 61/559,830, filed on Nov. 15, 2011.

(51) Int. Cl.
| | |
|---|---|
| A61K 38/13 | (2006.01) |
| C07K 7/64 | (2006.01) |
| C07K 1/00 | (2006.01) |
| C07K 1/30 | (2006.01) |
| A61K 9/00 | (2006.01) |

(52) U.S. Cl.
CPC .................. *A61K 38/13* (2013.01); *C07K 1/306* (2013.01); *C07K 7/645* (2013.01); *A61K 9/0048* (2013.01)

(58) Field of Classification Search
CPC .... C07K 1/1306; C07K 7/645; A61K 9/0048; A61K 38/13
See application file for complete search history.

(56) References Cited

U.S. PATENT DOCUMENTS

| | | | |
|---|---|---|---|
| 6,413,547 B1 * | 7/2002 | Bennett et al. | 424/489 |
| 2006/0205639 A1 | 9/2006 | Domb | |
| 2008/0299206 A1 | 12/2008 | Lee | |
| 2013/0023482 A1 * | 1/2013 | Gore et al. | 514/20.5 |

FOREIGN PATENT DOCUMENTS

| | | |
|---|---|---|
| GB | 2211848 A | 7/1989 |
| WO | 89-01772 | 3/1989 |
| WO | 2005-072701 | 8/2005 |
| WO | 2012-166610 | 12/2012 |

OTHER PUBLICATIONS

Bowen, P., Particle Size Distribution Measurement From Millimeters to Nanometers and From Rods to Platelets, Journal of Dispersion Science and Technology, 2002, 631-662, 23(5).

Zhou, Yunlong, Cyclosporine A: Solubilization, Solid Dispersion and Solid-State Transformation, A Thesis Submitted to the Faculty of Purdue University, Aug. 2000, 157 Pages.

Patent Cooperation Treaty, Notification of Transmittal of the International Search Report and the Written Opinion of the International Searching Authority, or the Declaration, Form PCT/ISA/220, Int. App. No. PCT/US2012/064985, Feb. 21, 2013.

* cited by examiner

*Primary Examiner* — Julie Ha
*Assistant Examiner* — Li Ni Komatsu
(74) *Attorney, Agent, or Firm* — Laura L. Wine; Joel B. German; Debra D. Condino

(57) ABSTRACT

Disclosed herein are methods of making cyclosporin A Form 2.

7 Claims, 9 Drawing Sheets

CYCLOSPORIN A FORM 2 AND METHOD OF MAKING SAME

CROSS-REFERENCE TO RELATED APPLICATION

This patent application is a divisional of U.S. patent application No. 13/676,339, filed Nov. 14, 2012, now issued as U.S. Pat. No. 8,796,221, which claims priority to U.S. Provisional Patent Application No. 61/559,830, filed Nov. 15, 2011, the entire contents of both applications are hereby incorporated by reference.

BACKGROUND

Disclosed herein is a method for making a new crystalline form of cyclosporin A.

Cyclosporin A

Cyclosporin A (CsA) is a cyclic peptide having the following chemical structure:

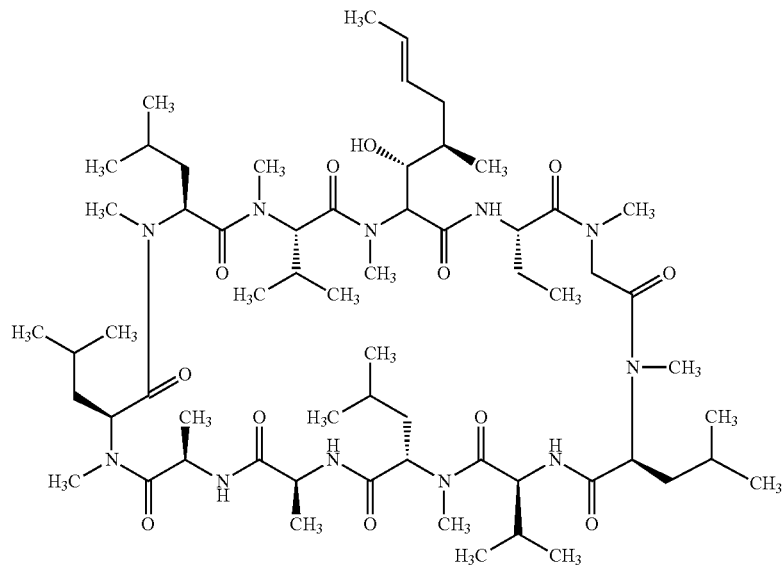 [SMILES: C/C=C/C[C@@H](C)[C@@H](O)C1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Its chemical name is cyclo[(E)-(2S,3R,4R)-3-hydroxy-4-methyl-2-(methylamino)-6-octenoylR-2-aminobutyryl-N-methylglycyl-N-methyl-Lleucyl-L-valyl-N-methyl-L-leucyl-L-alanyl-D-alanyl-N -methyl-L-leucyl-N-methyl-L-leucyl-N-methyl-L-valyl]. It is also known by the names cyclosporin, cyclosporine A, ciclosporin, and ciclosporin A. It is the active ingredient in RESTASIS® (Allergan, Inc., Irvine, California), an emulsion comprising 0.05% (w/v) cyclosporin. RESTASIS® is approved in the United States to increase tear production in patients whose tear production is presumed to be suppressed due to ocular inflammation associated with keratoconjunctivitis sicca.

Cyclosporin A is known to exist in an amorphous form, liquid crystal form, tetragonal crystalline form (Form 1), and an orthorhombic form (Form 3). The inventors describe here a method of making a new crystalline form, cyclosporin A Form 2.

DETAILED DESCRIPTION

Figure 1:
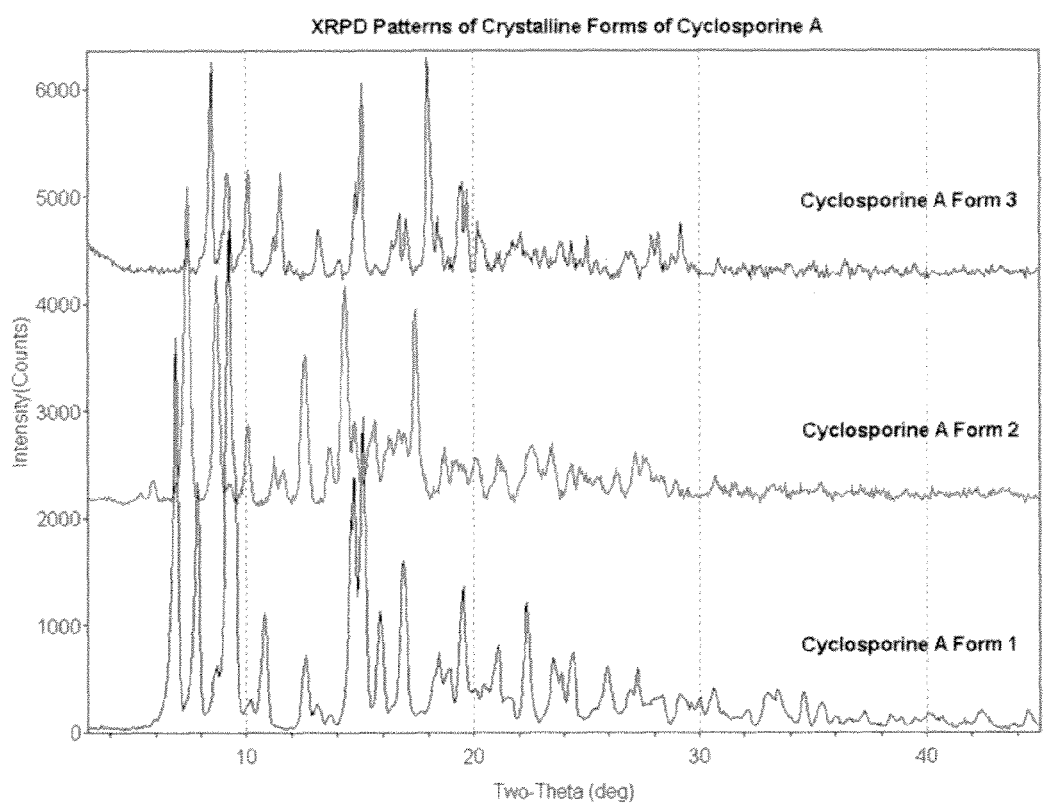
FIG. 1 depicts characteristic X-ray powder diffraction (XRPD) patterns of CsA in a new crystalline form (designated as Form 2 herein), tetragonal form (designated as Form 1 herein), and orthorhombic form (designated as Form 3 herein).
Figure 2:
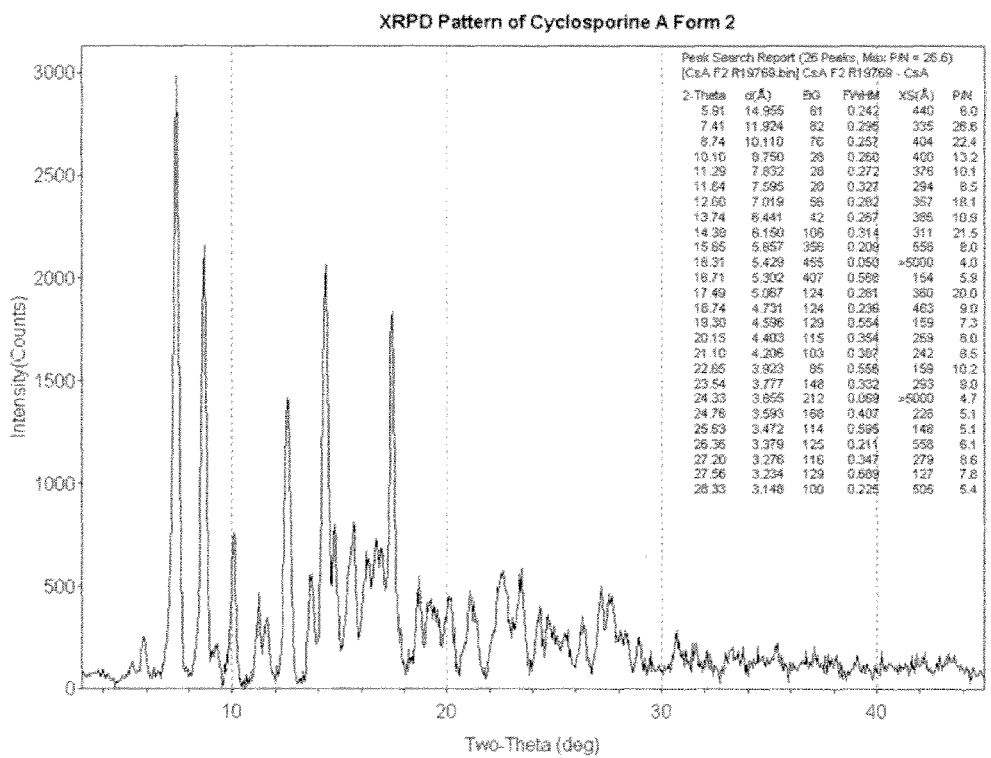
FIG. 2 depicts the XRPD diffractogram of CsA crystalline Form 2.

The XRPD pattern of CsA Form 2 differs significantly from the tetragonal form and orthorhombic form (FIG. 1). The major crystalline peaks for CsA form 2 appear at (2θ) when scanned by an X-ray diffractometer with X-ray source as Cu Kα radiation, λ=1.54 Å, at 30 kV/15 mA: 7.5, 8.8, 10.2, 11.3, 12.7, 13.8, 14.5, 15.6 and 17.5 (d-spacing in crystal lattice at about 11.8, 10.0, 8.7, 7.8, 7.0, 6.4, 6.1, 5.6 and 5.1 Å, respectively, FIG. 2). These major peaks are defined as those being unique to Form 2 relative to the orthorhombic or tetragonal forms; as well as, peaks having an intensity greater than 5 times the background.

In one embodiment, the new crystalline form (Form 2) of CsA is a nonstoichiometric hydrate of Cyclosporin A. In another embodiment, the crystalline Form 2 is represented by the formula:

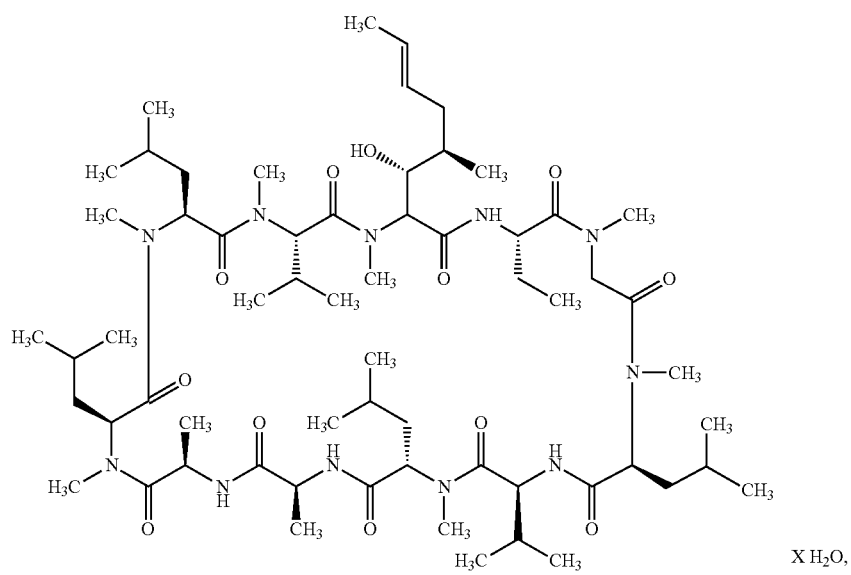 [SMILES: C/C=C/C[C@@H](C)[C@@H](O)C1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

X H₂O, wherein X is the number of molecules of water and varies from 0 to 3. In one embodiment, X in the above formula is 2.

Form 2 appears to be a kinetically stable form of CsA in aqueous suspensions. Suspensions containing Form 2 show no conversion to other known polymorphic or pseudomorphic forms upon storage. It has been found that Form 1 and the amorphous form convert to Form 2 in the presence of water.

The single crystal structure of the hydrate form of CsA Form 2 has been determined and the crystal structure parameters are listed in Table 2. These results indicate that Form 2 is unique compared to other known crystalline forms of cyclosporine A.

TABLE 1

| Crystal data and data collection parameters of crystal structure solution of CsA Form 2. | |
|---|---|
| formula | $C_{42}H_{115}N_{11}O_{14}$ |
| formula weight | 1238.67 |
| space group | P $2_1$ $2_1$ $2_1$ (No. 19) |
| a (Å) | 12.6390(5) |
| b (Å) | 19.7562(8) |
| c (Å) | 29.586(2) |
| volume (Å$^2$) | 7383.8(7) |
| Z | 4 |
| $d_{calc}$ (g cm$^{-2}$) | 1.114 |
| crystal dimensions (mm) | 0.27 × 0.18 × 0.12 |
| temperature (K) | 150 |
| radiation (wavelength in Å) | Cu $K_\alpha$ (1.54184) |
| monochromator | confocal optics |
| linear abs coef (mm$^{-1}$) | 0.640 |
| absorption correction applied | empirical$^2$ |
| transmission factors (min, max) | 0.60, 0.93 |
| diffractometer | Rigaku RAPID-II |
| h, k, l range | −13 to 13 −21 to 21 −32 to 21 |
| 2θ range (deg) | 5.38-115.00 |
| mosaicity (deg) | 1.31 |
| programs used | SHELXTL |
| $F_{000}$ | 2704.0 |
| weighting | $1/(\sigma^2(Fo^2) + (0.0845P)^2 + 0.0000P)$ where P = (Fo$^2$ + 2Fc$^2$)/3 |
| data collected | 37360 |
| unique data | 9964 |
| $R_{int}$ | 0.077 |
| data used in refinement | 9964 |
| cutoff used in R-factor calculations | $F_o^2 > 2.0$ s($F_o^2$) |
| data with I > 2.0 s(I) | 6597 |

TABLE 1-continued

| Crystal data and data collection parameters of crystal structure solution of CsA Form 2. | |
|---|---|
| number of variables | 834 |
| largest shift/esd in final cycle | 0.00 |
| R($F_o$) | 0.081 |
| $R_w(F_o^2)$ | 0.145 |
| goodness of fit | 1.037 |
| absolute structure determination | Flack parameter$^2$ (0.0(3)) |

Figure 9:
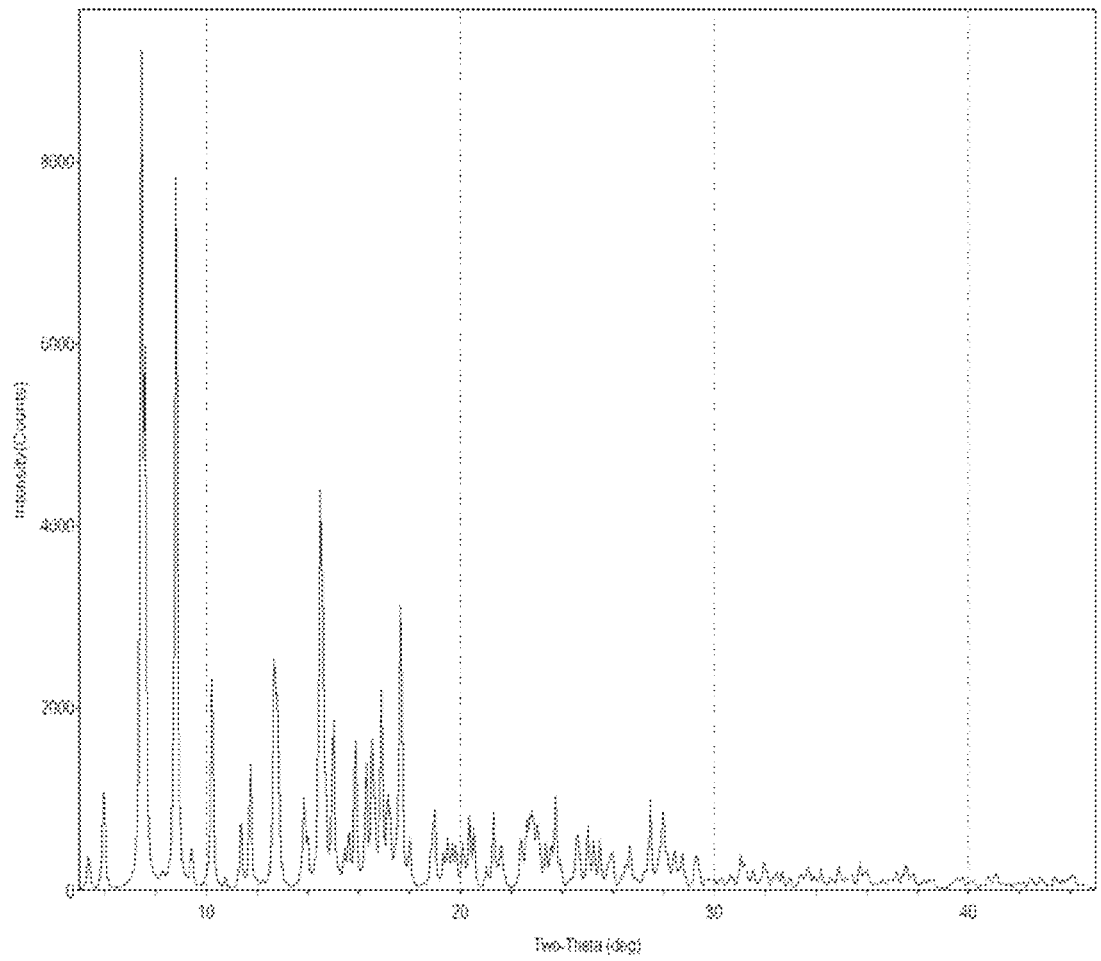
FIG. 9 shows the simulated XRPD pattern of cyclosporine A forms.

The asymmetric unit of this CsA Form 2 contains one cyclosporine A molecule and two water molecules. It is possible that any small molecule that can hydrogen bond to water could play the role of space filler, which would give a range of potential structures running from the orthorhombic dihydrate to distorted monoclinic dihydrate. The XRPD pattern calculated from the single-crystal structure is shown in FIG. 9 and it matches the experimental pattern shown in FIG. 2. These matching patterns further corroborate that Form 2 is a unique and pure crystalline form of cyclosporine A.

Figure 3:
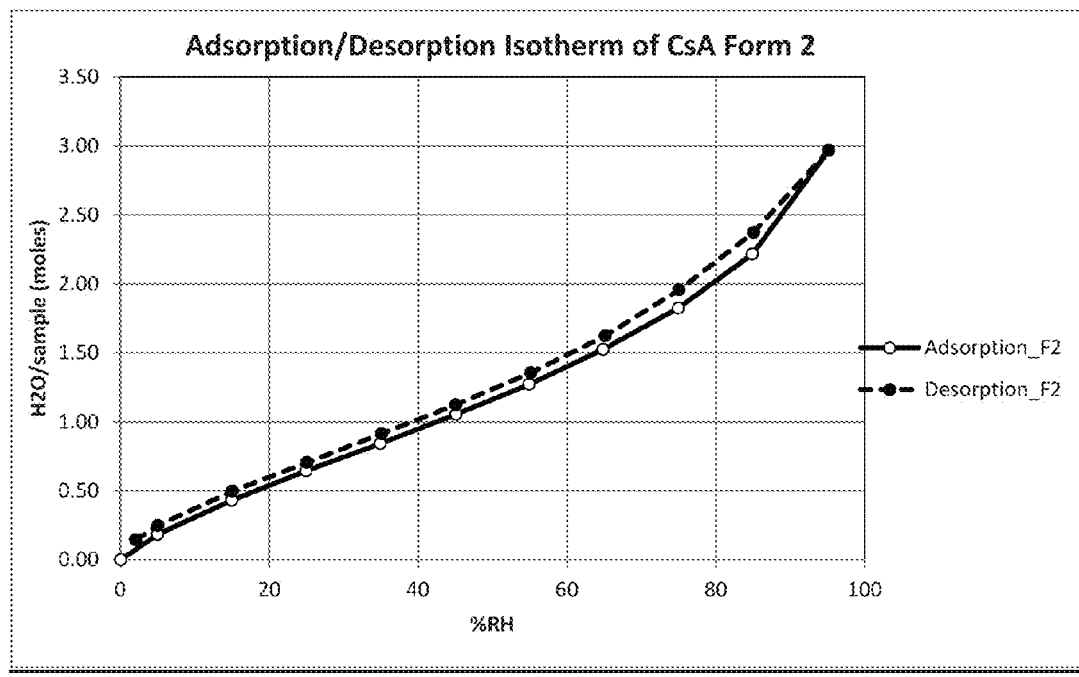
FIG. 3 depicts the water sorption/desorption profile of CsA Form 2.
Figure 4:
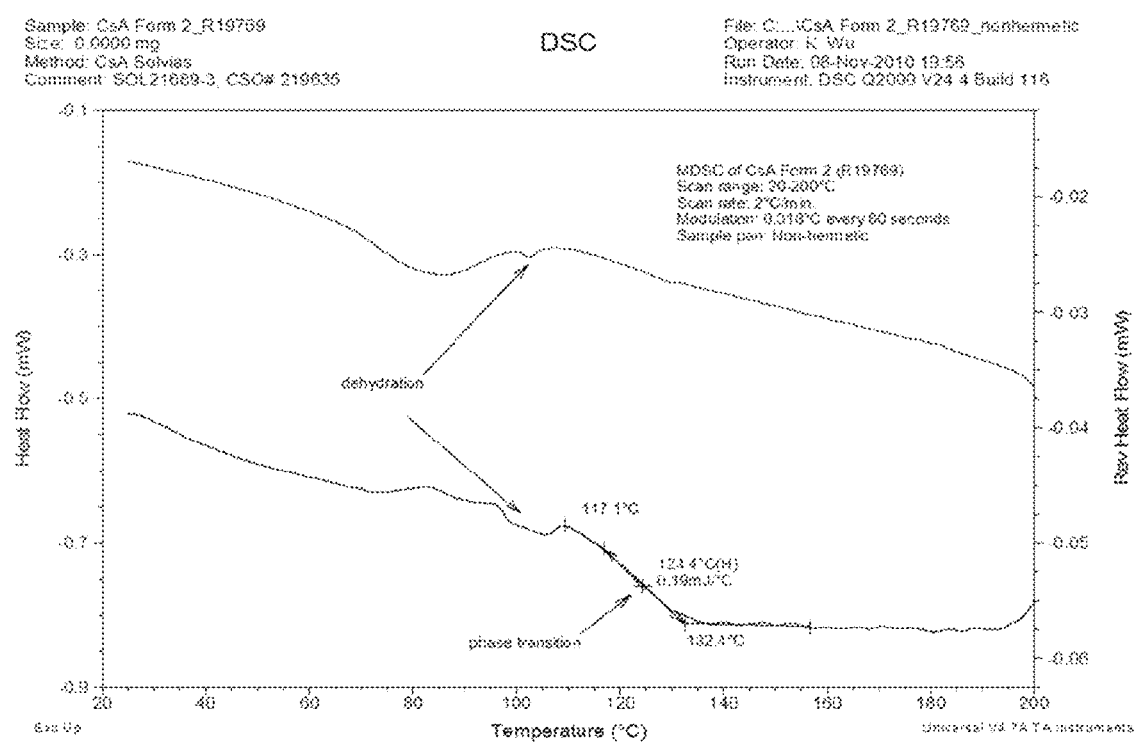
FIG. 4 depicts MDSC analysis of CsA Form 2 recovered from 0.04% formulation with 1% PS80.

Without wishing to be bound by theory, thermogravimetric analysis combined with KF titration and vapor sorption desorption analysis (VSA) suggest that CsA Form 2 is a non-stoichiometric hydrate of CsA. The vapor sorption analysis of Cyclosporine Form 2 indicates that water content in the new crystal form reversibly varies with relative humidity as shown in FIG. 3. Similar to the tetragonal form, the new CsA form undergoes a phase transition to a liquid crystal or amorphous form at 124.4° C. prior to melting as indicated by the modulated differential calorimetric (MDSC) analysis (FIG. 4).

Further details regarding CsA Form 2 may be found in U.S. patent application Ser. No. 13/480,710, the entire contents of which are incorporated by reference herein.

Methods of Obtaining Cyclosporin A Form 2

By Precipitation from Polysorbate 80

Cyclosporin A Form 2 may be obtained by suspending amorphous cyclosporin A in water containing Polysorbate 80 (polyoxyethylene sorbitan-mono-olleate), followed by heating the solution in to a temperature of between about 55° C. and about 75° C., and storing it at that temperature for at least between about 18 and about 48 hours, after which one removes the precipitate, cyclosporin A Form 2.

One can use in this method cyclosporin A at a concentration of between about 0.001% and about 10%. As used here, the term "about," when used in connection with a value, means a value that is reasonably close to the stated value.

One can therefore use in this method cyclosporin A at a concentration of about 0.001% (w/v), about 0.005% (w/v), about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v) cyclosporin A.

One can use in this method Polysorbate 80 at a concentration of between about 0.1% and 10%, such as about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 5% (w/v), about 6% (w/v), about 7% (w/v), about 8% (w/v), about 9% (w/v), or about 10% (w/v) Polysorbate 80.

After suspending the cyclosporin A in the Polysorbate 80, one can heat the solution to a temperature of between about 55° C. and about 75° C., such as about 55 ° C., about 56° C., about 57° C., about 58° C., about 59° C., about 60° C., about 61° C., about 62° C., about 63° C., about 64° C., about 65° C., about 66° C., about 66° C., about 67° C., about 68° C., about 69° C., about 70° C., about 71° C., about 72° C., about 73° C., about 74° C., or about 75° C.

One can store the heated solution at one of the foregoing temperatures for a length of time of between about 18 and about 48 hours, such as about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, or about 48 hours.

After preparing and heating the solution, and maintaining it at the desired temperature, the resulting precipitated solid may be recovered by any standard method, such as by vacuum filtration. Following the recovery, the precipitate may then be washed and dried. For example, it may be washed with water and then dried under vacuum at an elevated temperature (for example, about 40° C.), then at room temperature. Other washing and drying techniques may also be used.

Using Cyclosporin A Form 2 as a Seed Crystal

Cyclosporin A Form 2 may also be formed using cyclosporin A Form 2 as a seed crystal. In this method, one can suspend amorphous cyclosporin A in an aqueous solution of Polysorbate 80 and heat the solution as described above. One can then seed the solution with cyclosporin A Form 2, then maintain the solution at the temperatures and for the durations described above, constantly stirring the solution while doing so. At the conclusion of this process, one can then recover the precipitate as described above.

One can use between about 0.01 to about 1 g seed crystal/L water in this process. For example, one can use about 0.01 g/L, about 0.02 g/L, about 0.03 g/L, about 0.04 g/L, about 0.05 g/L, about 0.06 g/L, about 0.07 g/L, about 0.08 g/L, about 0.09 g/L, about 0.1 g/L, about 0.2 g/L, about 0.3 g/L, about 0.4 g/L, about 0.5 g/L, about 0.6 g/L, about 0.7 g/L, about 0.8 g/L, about 0.9 g/L, or about 1 g of seed crystal per liter of water.

One can heat the suspension of amorphous cyclosporin A seed crystal of cyclosporin A Form 2 to a temperature of between about 45° C. to about 65° C. before adding it to the solution, or one can leave the seed crystal at room temperature before adding it. For example, one can heat the seed crystal of cyclosporin A Form 2 to about 45° C., about 46° C., about 47° C., about 48° C. about, about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., or about 65° C. before adding it to the solution.

For example, one can suspend about 30 g cyclosporin A in a solution of 900 ml water containing 1% (w/v) Polysorbate 80. One can heat the solution to 65° C., and then seed it with 0.2 g of cyclosporin A Form 2 at a temperature of 52° C. The solution is stirred for about 22 hours at a temperature of between about 61° C. and 65° C. The resulting precipitate may be recovered as described above.

By Heating and Cooling in Certain Solvent Systems

In very general terms, cyclosporin A Form 2 may be obtained by 1) suspending cyclosporin A in either water, or in a solution of water and acetonitrile, 1,4-dioxane, or ethanol; 2) heating the suspension at a certain rate; 3) cooling the suspension at a certain rate; 4) repeating the cycle of heating and cooling; 5) and recovering the precipitate that results. The choice of solvent is critical: the inventors were able to find no structural feature or other property that predicted whether a solvent would or would not cause CsA Form 2 to form.

One can use in this embodiment cyclosporin A of the liquid crystal, tetragonal, or orthorhombic form, or one can use an amorphous form. The choice of starting material yields CsA Form 2 having very slightly different characteristics (see Figures X and Y), but the important point is that one can use different starting material and still obtain CsA Form 2.

In the first step of this method, one prepares a solution by suspending the desired starting material (that is, liquid crystal, tetragonal, orthorhombic form, or amorphous cyclosporin A) in water, or by suspending the starting material in acetonitrile, in 1,4-dioxane, or in ethanol, each dissolved in water. One can use in this step between about 0.01 to about 1 g starting material/L water. For example, one can use about 0.01 g/L, about 0.02 g/L, about 0.03 g/L, about 0.04 g/L, about 0.05 g/L, about 0.06 g/L, about 0.07 g/L, about 0.08 g/L, about 0.09 g/L, about 0.1 g/L, about 0.2 g/L, about 0.3 g/L, about 0.4 g/L, about 0.5 g/L, about 0.6 g/L, about 0.7 g/L, about 0.8 g/L, about 0.9 g/L, or about 1 g of starting material per liter of water. The desired solvent (acetonitrile, 1,4-dioxane, or ethanol) is added in that amount which results in the solution having a mole fraction of water of between about 0.75 and 1. For example, the solvent is added in an amount resulting in the solution having a mole fraction of about 0.75, about 0.76, about 0.77, about 0.78, about 0.79, about 0.80, about 0.81, about 0.82, about 0.83, about 0.84, about 0.85, about 0.86, about 0.87, about 0.88, about 0.89, about 0.90, about 0.91, about 0.92, about 0.93, about 0.94, about 0.95, about 0.96, about 0.97, about 0.98, about 0.99, and about 1.

In the second step of this method, one then heats the solution to a temperature of about 5° C. to about 50° C. at the rate of about 0.01° C. per minute to about 1° C. per minute. In one embodiment, one can heat the solution to a temperature of about 5° C. to about 10° C., about 10° C. to about 15° C., about 15° C. to about 20° C., about 20° C. to about 25° C., about 25° C. to about 30° C., about 30° C. to about 35° C., about 35° C. to about 40° C., about 40° C. to about 45° C., or about 45° C. to about 50° C. In another embodiment, one can heat the solution to a temperature of about 5° C. to about 15° C., about 15° C. to about 25° C., about 25° C. to about 35° C., about 35° C. to about 45° C., or about 40° C. to about 50° C. For example, one can heat the solution to a temperature of about 1° C., about 2° C., about 3° C., about 4° C., about 5° C., about 6° C., about 7° C., about 8° C., about 9° C., about 10° C., about 11° C., about 12° C., about 13° C., about 14 ° C., about 15° C., about 16° C., about 17° C., about 18° C., about 19° C., about 20° C., about 21° C., about 22° C., about 23° C., about 24° C., about 25° C., about 26° C., about 27 ° C., about 28° C., about 29° C., about 30° C., about 31° C., about 32° C., about 33° C., about 34° C., about 35° C., about 36° C., about 37° C., about 38° C., about 39° C., about 40 ° C., 41° C., about 42° C., about 43° C., about 44° C., about 45° C., about 46° C., about 47 ° C., about 48° C., about 49° C., or about 50° C.

In one embodiment, one heats the solution at a rate of about 0.01° C./min to about 0.05° C./min, about 0.05° C./min-0.1° C. per minute, about 0.1° C./min to about 0.2° C./min, about 0.2° C./min to about 0.3° C./min, about 0.3° C./min to about 0.4° C./min, about 0.4° C./min to about 0.5° C./min, about 0.5° C./min to about 0.6° C./min, about 0.6° C./min to about 0.7° C./min, about 0.7° C./min to about 0.8° C./min, about 0.8° C./min to about 0.9° C./min, or about 0.9° C./min to about 1° C./min. For example, one can heat the solution at the rate of about 0.01° C./min, about 0.02° C./min, about 0.03° C./min, about 0.04° C./min, about 0.05° C./min, about 0.06° C./min, about 0.07° C./min, about 0.08° C./min, about 0.09° C./min, about 0.1° C./min, about 0.2° C./min, about 0.3° C./min, about 0.4° C./min, about 0.5° C./min, about 0.6° C. /min, about 0.7° C./min, about 0.8° C./min, about 0.9° C./min, or about 1° C./min.

In the third step of this method, one then cools the solution to a temperature of between about 1° C. to about 22° C. In one embodiment, one can cool the solution to a temperature of about 1° C. to about 5° C., about 5° C. to about 10° C., about 10° C. to about 15° C., about 15° C. to about 20° C., or about 17° C. to about 22° C. In another embodiment, one can cool the solution to a temperature of about 1° C. to about 10° C., about 5° C. to about 15° C., about 10° C. to about 20° C., or about 15° C. to about 22° C. For example, one can cool the solution to a temperature of about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., or about 22° C.

The solution may be cooled at the same or different rate at which it is heated. In one embodiment, one cools the solution at a rate of about 0.01° C./min to about 0.05° C./min, about 0.05° C./min to 0.1° C. per minute, about 0.1° C./min to about 0.2° C. / min, about 0.2° C./min to about 0.3° C./min, about 0.3° C./min to about 0.4° C./min, about 0.4° C./min to about 0.5° C./min, about 0.5° C./min to about 0.6° C./min, about 0.6° C./min to about 0.7° C./min, about 0.7° C./min to about 0.8° C./min, about 0.8° C./min to about 0.9° C./min, or about 0.9° C./min to about 1° C./min. For example, one can cool the solution at the rate of about 0.01° C./min, about 0.02° C./min, about 0.03° C./min, about 0.04° C./min, about 0.05° C./min, about 0.06° C./min, about 0.07° C./min, about 0.08° C./min, about 0.09° C./min, about 0.1° C./min, about 0.2° C./min, about 0.3° C./min, about 0.4° C./min, about 0.5° C./min, about 0.6° C./min, about 0.7° C./min, about 0.8° C./min, about 0.9° C./min, or about 1° C./min.

One may then proceed to recover any precipitate that has formed, using the methods described above, or one may repeat the steps of heating and cooling, using the same or different temperatures and the same or different rates of heating and cooling. In one embodiment, one repeats the steps of heating and cooling once, that is, one first heats then cools the solution, then heats and cools the solution again. In another embodiment, one repeats the steps of heating and cooling two times, that is, one first heats then cools the solution, then heats and cools the solution a second time, then heats and cooling the solution a third time. In another embodiment, one repeats the steps of heating and cooling three times, that is, one first heats then cools the solution, then heats and cools the solution a second time, then heats and cooling the solution a third time, and then heats and cooling the solution a fourth time. During each of the heating steps, one can heat the solution to the same or different temperature, and at the same or different rate; likewise, during each of the cooling steps, one can heat the solution to the same or different temperature, and at the same or different rate.

In one embodiment, one begins to cool the solution immediately after heating the solution to the desired temperature. In another embodiment, one maintains the solution at the heated temperature for between about 0 and about 25 hours before beginning to cool it. For example, one can maintain the solution at the heated temperature for about 0 to about 5 hours, about 5 to about 10 hours, about 10 to about 15 hours, about 15 to about 20 hours, or about 20 to 25 hours; in another embodiment, one can maintain the solution at the heated temperature for about 0 to about 10 hours, about 5 to about 15 hours, about 10 to about 20 hours, or about 15 to about 25 hours. For example, one can maintain the solution at the heated temperature for about 0.5 hours, about 1 hours, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours.

If repeating a heating-cooling cycle, one can immediately heat the solution after it has cooled to the desired temperature, or one can maintain the solution at the cooled temperature for between about 0 and about 24 hours before beginning to heat it again. For example, one can maintain the solution for about 0 to about 5 hours, about 5 to about 10 hours, about 10 to about 15 hours, about 15 to about 20 hours, or about 20 to 25 hours; in another embodiment, one can maintain the solution at the cooled temperature for about 0 to about 10 hours, about 5 to about 15 hours, about 10 to about 20 hours, or about 15 to about 25 hours. For example, one can maintain the solution at the cooled temperature for about 0.5 hours, about 1 hours, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours At the conclusion of the heating and cooling cycle, one can hold the solution at the final, cooled temperature for about 0 to about 24 hours before recovering the precipitate as described above.

EXAMPLES

The invention is further illustrated by way of the following examples.

Example 1

Cyclosporin A (CsA), either of the amorphous, tetragonal (F1), or orthorhombic form, was suspended in water, acetonitrile, dioxane, or ethanol, as described in Table 1, below:

TABLE 1

Cyclosporin suspension used to make cyclosporin form 2

| CsA FORM | SOLVENT 1 | SOLVENT 2 | MOLE FRACTION OF WATER |
|---|---|---|---|
| amorphous | Water | acetonitrile | 0.87 |
| F1 | Water | acetonitrile | 0.87 |
| F3 | Water | acetonitrile | 0.87 |
| F1 | water | none | 1.00 |
| F1 | water | dioxane | 0.90 |
| F1 | Water | Ethanol | 0.89 |

Figure 5:
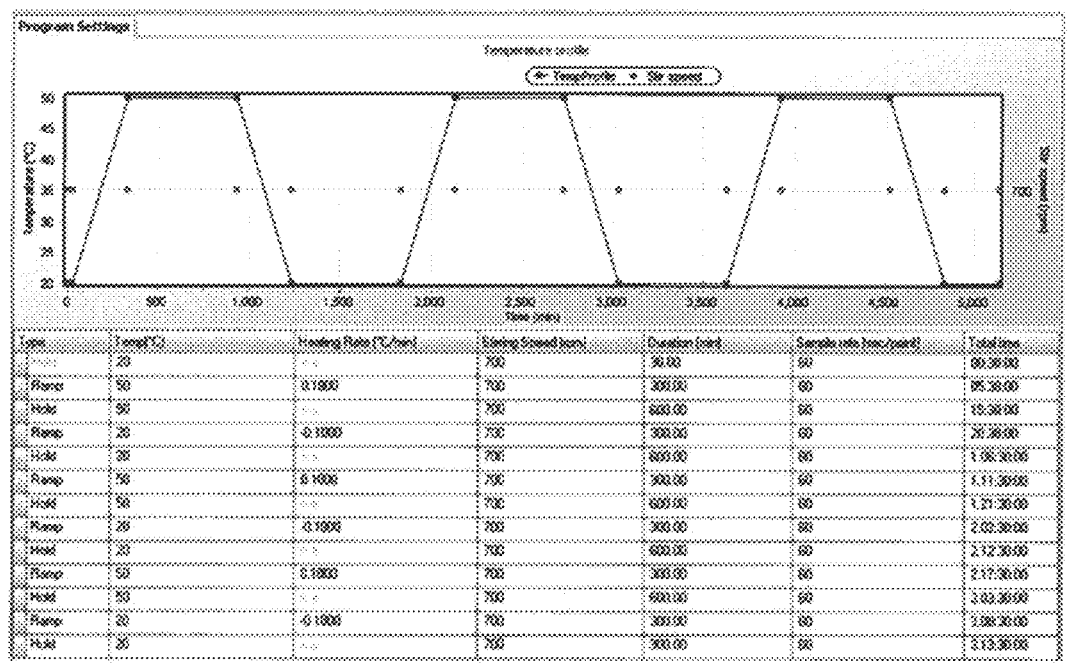
FIG. 5 depicts a cycle of heating and cooling used to generate the CsA Form 2 generated by a method according to the invention.

Each of the above solutions was heated to 50° C. at a rate of 0.1° C. per minute, and maintained at that temperature for 600 min; the solution was then cooled to 20° C. at the same rate, and held at that temperature for 300 min; this cycle of heating and cooling was repeated twice more, as illustrated in FIG. 5 and summarized at Table 2:

TABLE 2

Thermocycling profile

| Step | Temp (° C.) | Heating Rate (° C./min) | Duration (min) | Total time |
|---|---|---|---|---|
| Hold | 20 | — | 30.00 | 00:30:00 |
| Ramp | 50 | 0.1000 | 300.00 | 05:30:00 |
| Hold | 50 | — | 600.00 | 15:30:00 |
| Ramp | 20 | −0.1000 | 300.00 | 20:30:00 |
| Hold | 20 | — | 600.00 | 1.06:30:00 |
| Ramp | 50 | 0.1000 | 300.00 | 1.11:30:00 |
| Hold | 50 | — | 600.00 | 1.21:30:00 |
| Ramp | 20 | −0.1000 | 300.00 | 2.02:30:00 |
| Hold | 20 | — | 600.00 | 2.12:30:00 |
| Ramp | 50 | 0.1000 | 300.00 | 2.17:30:00 |
| Hold | 50 | — | 600.00 | 3.03:30:00 |
| Ramp | 20 | −0.1000 | 300.00 | 3.06:30:00 |
| Hold | 20 | — | 300.00 | 3.13:30:00 |

Figure 6:
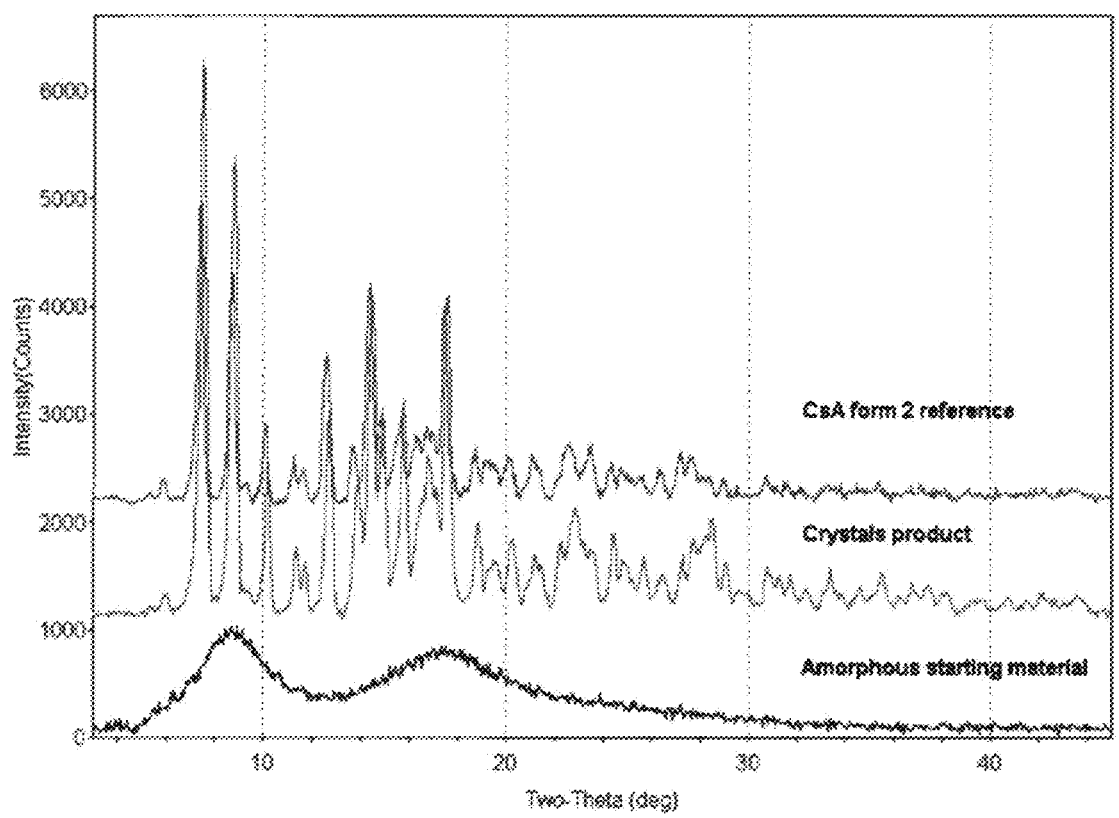
FIG. 6 shows the x-ray diffraction pattern (XRPD) of CsA Form 2 obtained according to a method of the invention, using amorphous cyclosporin A as the starting material.
Figure 7:
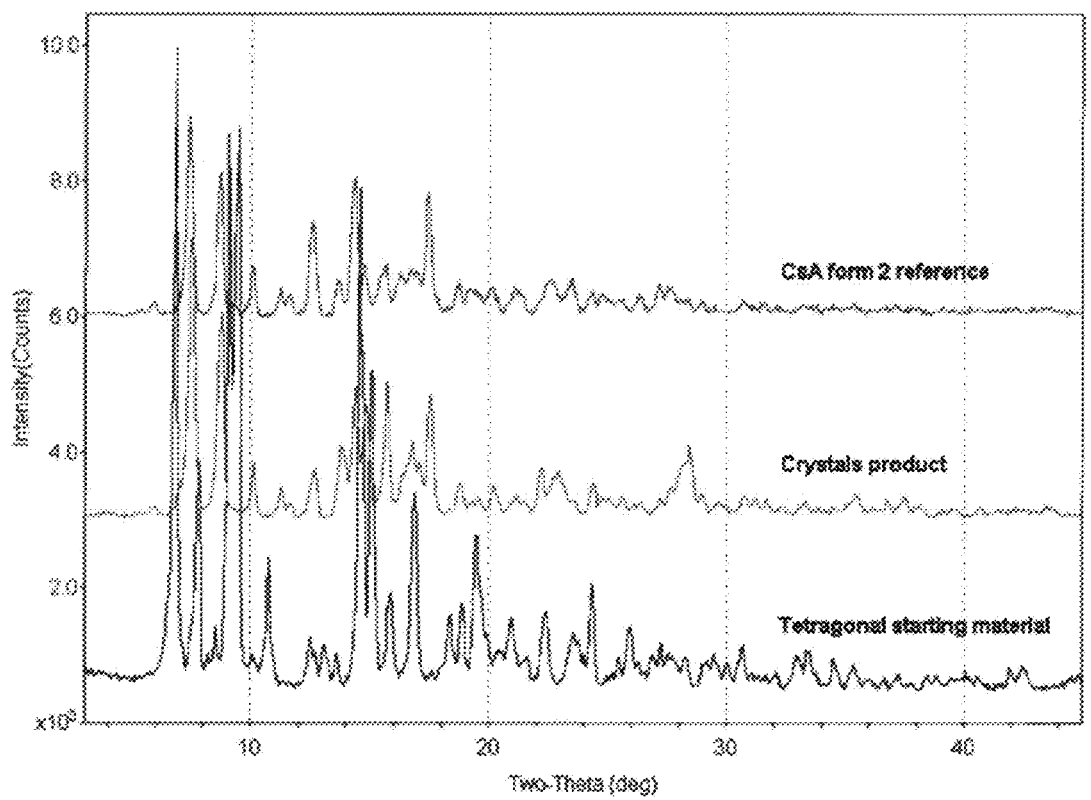
FIG. 7 shows the XRPD of CsA Form 2 obtained according to a method of the invention, using tetragonal cyclosporin A as the starting material.
Figure 8:
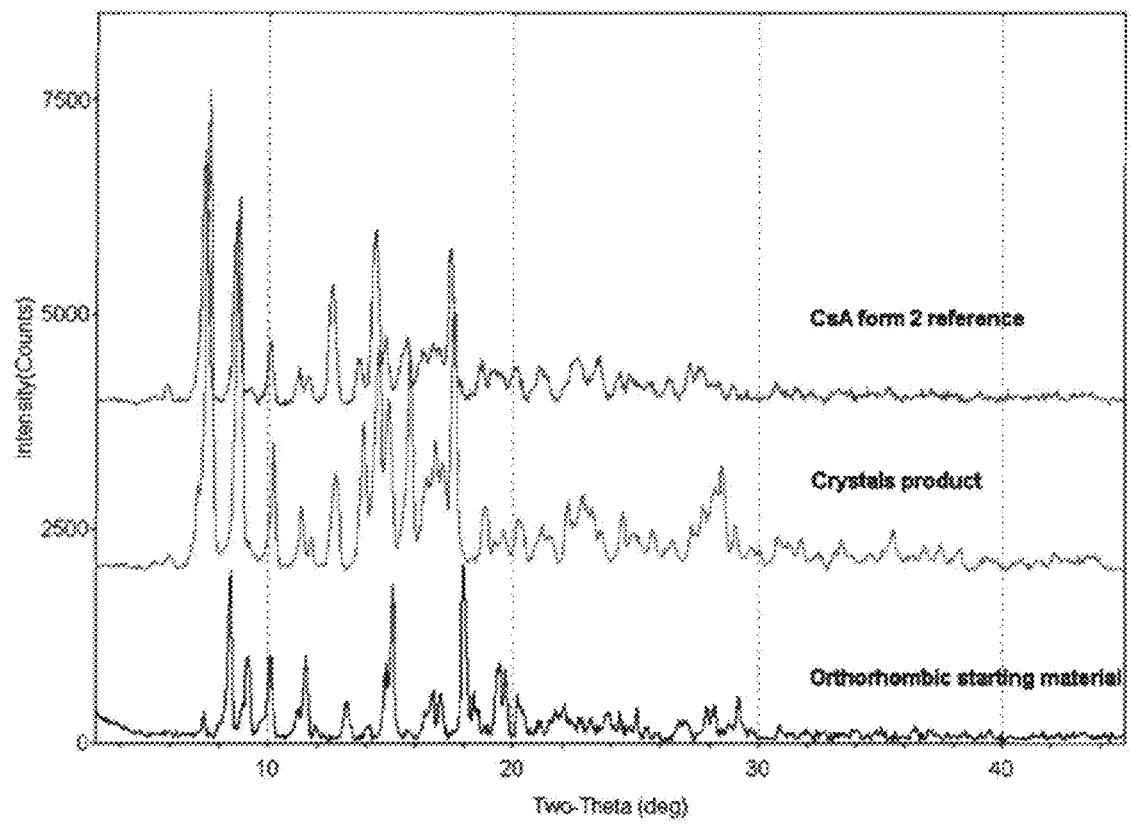
FIG. 8 shows the XRPD of CsA Form 2 obtained according to a method of the invention, using orthorhombic cyclosporin A as the starting material.

The x-ray powder diffraction pattern (XRPD) of cyclosporin A form 2 thus obtained, using amorphous cyclosporin A as the starting material, is illustrated at FIG. 6; the XRPD of cyclosporin A form 2 obtained using tetragonal cyclosporin A as the starting material is illustrated at FIG. 7; the XRPD of cyclosporin A form 2 obtained using orthorhombic cyclosporin A as the starting material is illustrated at FIG. 8. XRPD patterns of CsA forms were obtained using a Rigaku MiniFlex X-ray diffractometer (Cu $K_\alpha$ radiation, $\lambda$=1.54 Å, at 30 kV and 15 mA). The instrument was calibrated with a silicon standard with a reference peak at 28.44° (2-theta). The X-ray diffraction experiments were performed from 3° to 45° (2-theta) at a scan rate of 0.5° or 1° (2-theta) per minute and a step width of 0.05° (2-theta).

Experimental conditions that did not produce cyclosporin A Form 2 are shown below in Table 3:

TABLE 3

Experimental conditions that did not produce cyclosporin A Form 2

| # | CsA Form | CsA Weight (mg) | Solvent 1 | Solvent 2 | Volume (µL) 1 | Volume (µL) 2 | Final Form | Mole fraction of water |
|---|---|---|---|---|---|---|---|---|
| 1 | Amorphous | 53.77 | water | acetone | 100 | 42 | F1 + F2 | 0.91 |
| 2 | Amorphous | 61.70 | water | ethylene glycol | 100 | 42 | amorphous | 0.88 |
| 4 | Amorphous | 41.17 | water | n/a | 100 | n/a | amorphous | 1.00 |
| 5 | F1 | 65.74 | water | acetone | 100 | 42 | F1 + F2 | 0.91 |
| 6 | F1 | 74.51 | water | ethylene glycol | 100 | 42 | F1 | 0.88 |
| 8 | F1 | 68.59 | water | n/a | 100 | n/a | amorphous | 1.00 |
| 9 | F3 | 49.70 | water | acetone | 100 | 42 | F3 | 0.91 |
| 10 | F3 | 69.45 | water | ethylene glycol | 100 | 42 | F3 | 0.88 |
| 12 | F3 | 70.87 | water | n/a | 100 | n/a | F3 | 1.00 |
| 15 | F1 | 43.07 | water | methanol | 100 | 42 | amorphous + F2 | 0.84 |

Methods of Treatment

Compositions of the invention may be used to treat any condition of the eye which is known to be amenable to topical treatment with cyclosporin A (such as with RESTASIS®) at the concentrations stated here. For example, compositions of the invention may be used to treat patients suffering from dry eye, to treat blepharitis and meibomian gland disease, to restore corneal sensitivity that has been impaired due to refractive surgery on the eye, to treat allergic conjunctivitis and atopic and vernal keratoconjunctivitis, and to treat ptyregia, conjunctival and corneal inflammation, keratoconjuntivitis, graft versus host disease, post-transplant glaucoma, corneal transplants, mycotic keratitis, Thygeson's superficial punctate keratitis, uveitis, and Theodore's superior limbic keratoconjunctivitis, among other conditions.

The International Dry Eye Workshop (DEWS) defines dry eye as "a multifactorial disease of the tears and ocular surface that results in symptoms of discomfort, visual disturbance, and tear film instability with potential damage to the ocular surface, accompanied by increased osmolarity of the tear film and inflammation of the ocular surface." It includes those conditions, such as keratoconjunctivitis sicca, that are caused by tear deficiency or excessive evaporation of tears.

Blepharitis is a chronic disorder producing inflammation of the anterior and posterior lid margin, with involvement of skin and its related structures (hairs and sebaceous glands), the mucocutaneous junction, and the meibomian glands. It can also affect the conjunctiva, tear film, and the corneal surface in advanced stages and may be associated with dry eye. Blepharitis is commonly classified into anterior or posterior blepharitis, with anterior affecting the lash bearing region of the lids, and posterior primarily affecting the meibomian gland orifices.

Meibomian gland disease most often occurs as one of three forms: primary meibomitis, secondary meibomitis, and meibomian seborrhea. Meibomian seborrhea is characterized by excessive meibomian secretion in the absence of inflammation (hypersecretory meibomian gland disease). Primary meibomitis, by contrast, is distinguished by stagnant and inspissated meibomian secretions (obstructive hypersecretory meibomian gland disease). Secondary meibomitis represents a localized inflammatory response in which the meibomian glands are secondarily inflamed in a spotty fashion from an anterior lid margin blepharitis.

Impaired corneal sensitivity often occurs after refractive surgery, such as photorefractive keratectomy, laser assisted sub-epithelium keratomileusis (LASEK), EPI-LASEK, customized transepithelial non-contact ablation, or other procedures in which the corneal nerves are severed. Impaired corneal sensitivity may also occur after viral infection, such as by HSV-1, HSV-2, and VZV viruses. Patients with impaired corneal sensitivity often complain that their eyes feel dry, even though tear production and evaporation may be normal, suggesting that "dryness" in such patients is actually a form of corneal neuropathy that results when corneal nerves are severed by surgery or inflamed after viral infection.

Allergic conjunctivitis is an inflammation of the conjunctiva resulting from hypersensitivity to one or more allergens. It may be acute, intermittent, or chronic. It occurs seasonally, that is, at only certain time of the year, or it occurs perennially, that is, chronically throughout the year. Symptoms of seasonal and perennial allergic conjunctivitis include, in addition to inflammation of the conjunctiva, lacrimation, tearing, conjunctival vascular dilation, itching, papillary hyperlasia, chemosis, eyelid edema, and discharge from the eye. The discharge may form a crust over the eyes after a night's sleep.

Atopic keratoconjunctivitis is a chronic, severe form of allergic conjunctivitis that often leads to visual impairment. Symptoms include itching, burning, pain, redness, foreign body sensation, light sensitivity and blurry vision. There is often a discharge, especially on awakening from a night's sleep; the discharge may be stringy, ropy, and mucoid. The lower conjunctiva is often more prominently affected than the upper conjunctiva. The conjunctiva may range from pale, edematous, and featureless to having the characteristics of advanced disease, including papillary hypertrophy, subepithelial fibrosis, formix foreshortening, trichiasis, entropion, and madurosis. In some patients the disease progresses to punctate epithelial erosions, corneal neovascularization, and other features of keratopathy which may impair vision. There is typically goblet cell proliferation in the conjunctiva, epithelial pseudotubular formation, and an increased number of degranulating eosinophils and mast cells in the epithelium. CD25+ T lymphocytes, macrophages, and dendritic cells (HLA-DR.sup.+, HLA-CD1+) are significantly elevated in the substantia propria.

Like atopic keratoconjunctivitis, vernal keratoconjunctivitis is a severe form of allergic conjunctivitis, but it tends to affect the upper conjunctiva more prominently than the lower. It occurs in two forms. In the palpebral form, square, hard, flattened, closely packed papillae are present; in the bulbar (limbal) form, the circumcorneal conjunctiva becomes hypertrophied and grayish. Both forms are often accompanied by a mucoid discharge. Corneal epithelium loss may occur, accompanied by pain and photophobia, as may central corneal plaques and Trantas' dots.

What is claimed is:

1. A method for making cyclosporin A form 2, the method comprising the steps of:
    a) preparing a suspension of cyclosporin A in a solvent comprising an ingredient selected from the group consisting of acetonitrile, 1,4-dioxane, and ethanol;
    b) heating the suspension;
    c) adding cyclosporin A form 2 to the suspension;
    d) stirring the suspension; and
    e) isolating cyclosporin A form 2 from the suspension.

2. The method of claim 1, wherein the step of heating the suspension comprises heating the suspension at a temperature of between about 40°C. and 70°C.

3. The method of claim 2, wherein the step of heating the suspension comprises heating the suspension at a temperature of between about 60°C. and 65°C.

4. The method of claim 1, wherein the step of stirring the suspension comprises stirring the suspension at a temperature of between about 20°C. and 70°C.

5. The method of claim 4, wherein the step of stirring the suspension comprises stirring the suspension at a temperature of between about 60°C. and 65°C.

6. The method of claim 5, wherein the step of stirring the suspension comprises stirring the suspension for between about 24 hours_and about 72 hours.

7. The method of claim 5, wherein the step of stirring the suspension comprises stirring the suspension for between about 22 hours_and about 23 hours.

* * * * *